United States Patent
Dietrich et al.

(10) Patent No.: US 7,041,313 B1
(45) Date of Patent: May 9, 2006

(54) ORAL ADMINISTRATION FORM FOR PYRIDIN-2-YLMETHYLSULFINYL-1H-BENZIMIDAZOLES

(75) Inventors: Rango Dietrich, Constance (DE); Hartmut Ney, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 09/762,302

(22) PCT Filed: Aug. 7, 1999

(86) PCT No.: PCT/EP99/05724

§ 371 (c)(1),
(2), (4) Date: Feb. 8, 2001

(87) PCT Pub. No.: WO00/09092

PCT Pub. Date: Feb. 24, 2000

(30) Foreign Application Priority Data

Aug. 12, 1998 (EP) .................................. 98115141

(51) Int. Cl.
*A61K 9/48* (2006.01)
*A61K 9/14* (2006.01)
*A61K 9/16* (2006.01)

(52) U.S. Cl. ...................... 424/451; 424/463; 424/489; 424/490

(58) Field of Classification Search ................ 424/464, 424/465, 451, 468, 463, 489, 490
See application file for complete search history.

(56) References Cited

U.S. PATENT DOCUMENTS 4,786,505 A * 11/1988 Lovgren et al. ............. 424/479
5,260,069 A * 11/1993 Chen .......................... 424/451

FOREIGN PATENT DOCUMENTS

| DE | 42 19 390 | 12/1992 | |
|---|---|---|---|
| EP | 0 519 365 | 12/1992 | |
| EP | 0 526 862 | 2/1993 | |
| EP | 0 793 959 | 9/1997 | |
| WO | 97/02020 | * | 1/1997 |
| WO | 97/25979 | | 7/1997 |

\* cited by examiner

*Primary Examiner*—Humera N. Sheikh
(74) *Attorney, Agent, or Firm*—Nath & Associates PLLC; Joshua B. Goldberg; Sheldon M. McGee

(57) ABSTRACT

The invention relates to an oral administration form for pyridin-2-ylmethylsulfinyl-1H-benzimidazoles and their salts, which comprises the active compound together with tablet disintegrants and is provided with a film coating customary per se for sustained-release compositions.

36 Claims, No Drawings

ORAL ADMINISTRATION FORM FOR PYRIDIN-2-YLMETHYLSULFINYL-1H-BENZIMIDAZOLES

This application is a 371 of PCT/EP99/05724 filed Aug. 7, 1999 and claims priority to EPO Application No. 98115141.8 filed Aug. 12, 1998

SUBJECT OF THE INVENTION

The present invention relates to a novel oral administration form for pyridin-2-ylmethylsulfinyl-1H-benzimidazoles.

PRIOR ART

Pyridin-2-ylmethylsulfinyl-1H-benzimidazoles and compounds structurally related to these, such as are disclosed, for example, in EP-A-005129, EP-A-0166287, EP-A-0174726, EP-A-0268956, DE-A-3531487 and EP-A-0434999, have, on account of their $H^+K^+$ATPase-inhibiting action, considerable importance in the therapy of diseases which are due to increased gastric acid secretion. Examples of active compounds from this group which are commercially available or in an advanced stage of clinical testing are 5-methoxy-2-[(4-methoxy-3,5-dimethyl-2-pyridinyl)methylsulfinyl]-1H-benzimidazole (INN: omeprazole), 5-methoxy-2-[(S)-(4-methoxy-3,5-dimethyl-2-pyridinyl)methylsulfinyl]-1H-benzimidazole (prop. INN: esomeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoroethoxy)-2-pyridinyl)methyl-sulfinyl]-1H-benzimidazole (INN: lansoprazole), 2-{[4-(3-methoxypropoxy)-3-methylpyridin-2-yl]methyl-sulfinyl}-1H-benzimidazole (INN: rabeprazole), 2-[2-(N-isobutyl-N-methylamino)benzylsulfinyl]benzimidazole (leminoprazole) and 2-(4-methoxy-6,7,8,9-tetrahydro-5H-cyclohepta[b]pyridin-9-ylsulfinyl)-1H-benzimidazole (nepaprazole).

A common characteristic of the abovementioned pyridin-2-ylmethylsulfinyl-1H-benzimidazoles is the acid sensitivity—which is finally indispensable for their efficacy—of these active compounds, which is seen in their strong tendency to decompose in a neutral and, in particular, acidic environment, strongly colored decomposition products being formed.

In the past, there have been considerable efforts, despite the acid sensitivity of the pyridin-2-ylmethylsulfinyl-1H-benzimidazoles, to obtain stable and storable oral administration forms which contain these compounds. There have likewise been efforts to obtain custom administration forms for pyridin-2-ylmethylsulfinyl-1H-benzimidazoles for certain application purposes.

European Patent EP-B1-244 380 claims an oral administration form for certain pyridin-2-ylmethylsulfinyl-1H-benzimidazoles in which the active compound present in the tablet or pellet core is protected from the gastric acid by an enteric coating, a water-soluble intermediate layer which is intended to protect the core and acidic coating from one another additionally being situated between the active compound core and enteric coating.

The protection of the pyridin-2-ylmethylsulfinyl-1H-benzimidazoles from gastric acid by application of an enteric coating can be regarded as the method of choice up to now when oral administration forms for this class of active compound are involved. The enteric coatings, whose resistance to gastric juice is based on the fact that free acidic groups (in particular carboxyl groups) are present in a polymer, must be separated, however, from the acid-sensitive active compound cores by suitable measures. This is carried out by application or production of a protective intermediate layer composed in whatever way (see, for example, EP-B1-589 981, WO-A-9601624, WO-A-9623500, WO-A-9624338, WO-A-9402140, WO-A-9712580 and WO-A-9800115).

DESCRIPTION OF THE INVENTION

Surprisingly, it has now been found that an enteric coating for pyridin-2-ylmethylsulfinyl-1H-benzimidazoles is unnecessary if the coating used instead of it is designed so that the active compound is released only after a defined time, namely after gastric passage. Furthermore, it has surprisingly been found that, with a suitable design of the core comprising the active compound, the release of the active compound—once it has commenced—takes place within a short space of time, so that a rapidly rising and high active compound blood level is achieved.

The invention thus relates to an oral administration form for pyridin-2-ylmethylsulfinyl-1H-benzimidazoles and their salts, which comprises the active compound together with tablet disintegrants and is provided with a film coating which is customary per se for sustained-release compositions.

Possible oral administration forms are, for example, pellets, microtablets, minitablets or in particular tablets, if desired dispensed in capsules.

Suitable pyridin-2-ylmethylsulfinyl-1H-benzimidazoles within the meaning of the invention are, for example, omeprazole, esomeprazole, lansoprazole, rabeprazole, leminoprazole, nepaprazole and in particular pantoprazole.

Salts of the pyridin-2-ylmethylsulfinyl-1H-benzimidazoles which may be mentioned primarily are the salts with bases, in particular the sodium, potassium, calcium and magnesium salt. The pantoprazole sodium salts, in particular the pantoprazole sodium sesquihydrate, is particularly preferred.

Possible tablet disintegrants are the customary agents known to the person skilled in the art. Examples which may be mentioned are certain cellulose derivatives (e.g. sodium cellulose glycolate and Tyloses), starch, compositions based on sodium carboxymethylcellulose and potato starch (e.g. Primojel), sodium carboxymethylstarch (e.g. Explotab), bentonite, sodium alginate or pectin, but in particular chemically indifferent agents such as crosslinked polyvinylpyrrolidone (e.g. Crospovidone). The content of tablet disintegrant is customarily between 2 and 10% by weight based on the entire core. Depending on the type of tablet disintegrant, however, larger contents can also be used, in the case of Crospovidone, for example, 20–35% by weight.

In addition to the tablet disintegrant, if desired the tablet cores contain further auxiliaries and fillers or binders. Auxiliaries used are, in particular, lubricants and release agents. Mention may be made here, for example, of calcium salts of higher fatty acids, such as, for example, calcium stearate. Binders which may be mentioned are, in particular, polyvinylpyrrolidone and/or hydroxypropylmethylcellulose and, if desired, mannitol, which is additionally preferred as a filler.

To increase the stability of the tablet cores, it has proven advantageous to employ the pyridin-2-ylmethylsulfinyl-1H-benzimidazoles in the form of their salts and/or with addition of one or more physiologically tolerable inorganic compounds having a basic reaction. Mention may be made here, for example, of the pharmacologically tolerable alkali metal, alkaline earth metal or earth metal salts of weak acids and the pharmacologically tolerable hydroxides and oxides of alkaline earth metals and earth metals. A base to be emphasized by way of example which may be mentioned is sodium carbonate.

Film coatings customary for sustained-release compositions which may be mentioned are membranes made of plastics having a low swelling power in water, in which small soluble particles are embedded, or in particular those swellable plastic membranes which contain a small proportion of a suitable salt which determines the permeability of the film coating.

Plastics suitable for the construction of the membranes are those which are water-insoluble and physiologically tolerable. Plastics having a low swelling power in water are understood for the purposes of the present invention as meaning, for example, those which absorb not more than 5% by weight of water in aqueous medium. For this, cellulose ethers and cellulose esters are regarded as particularly suitable. In addition, suitable plastics are also polymers such as polyvinyl chloride. Swellable plastics which may be mentioned are, in particular, copolymers of acrylic and methacrylic acid esters.

Small soluble particles which may be mentioned are, for example, lactose crystals, which are preferably employed in micronized form. The particle size is expediently less than 20 μm, preferably less than 10 μm. The ratio of plastic to soluble particles can be varied within wide limits. A weight ratio of plastic to soluble particles of approximately 2:1 to 1:3 is preferred. A weight ratio of 4:3 to 4:5 is particularly preferred.

Salts suitable for the swellable plastic membranes which may be mentioned are, for example, ammonium salts, in particular quaternary ammonium salts. In a particular embodiment of plastic membranes, some of the ester groups of a copolymer of acrylic and methacrylic acid esters are ester groups having quaternary ammonium structures. An example of such copolymers having quaternary ammonium groups which may be mentioned is trimethylammonium methyl methacrylate chloride (e.g. Eudragit RL or Eudragit RS from Röm).

The release time of the pyridin-2-ylmethylsulfinyl-1H-benzimidazoles can be controlled within a wide range by variation of the composition of the membrane and/or by variation of the layer thickness of the membrane. Thus, release is effected at an earlier time by lowering the layer thickness of the membrane, by increasing the proportion of soluble particles, by use of the soluble particles in a more coarse-grained form or, in the case of the swellable plastic membranes, by increasing the proportion of a suitable salt (e.g. higher proportion of quaternary ammonium groups in the copolymer of acrylic and methacrylic acid esters).

The application of the membrane to the tablet cores is carried out in a manner known per se, in particular by one of the customary spraying techniques. For this, a solution of the plastic or plastic mixture intended for the membrane is prepared in a solvent or in a solvent mixture or preferably an aqueous dispersion of the plastic or plastic mixture. The soluble, micronized particles are suspended in the solution before the spraying. If necessary, the suspension is stirred during the spraying in order to prevent settling of the suspended particles. In the case of the preferred procedure using aqueous dispersions, the salts responsible for the permeability of the plastic are already contained in the plastic itself in the form of quaternary ammonium groups. In the case of application of the membrane from an aqueous dispersion, it is also possible to work under alkaline conditions.

The membrane can contain the customary auxiliaries, such as plasticizers, wetting agents, colorants and antiadherents. Pharmacologically tolerable plasticizers such as, for example, polyethylene glycols, paraffins, glycerol or propylene glycol are suitable. Wetting agents may be necessary if the coating is to be dyed with dye lakes. Sorbitol fatty acid esters or salts of dioctylsulfosuccinic acid, for example, are suitable. Antiadherents which may be mentioned are, in particular, calcium stearate or talc.

With respect to the preparation and construction of the tablet cores reference is made, for example, to the embodiments in European Patent EP-81-589 981.

The following examples of administration forms according to the invention explain the invention in greater detail without restricting it.

EXAMPLES

Example 1

Tablets

| A. Tablet cores with 10 mg of active compound | | |
|---|---|---|
| | Ingredients | per core |
| (a) | pantoprazole Na × 1.5 H$_2$O | 11.28 mg |
| (b) | sodium carbonate, anhydrous | 2.50 mg |
| (c) | mannitol | 10.68 mg |
| (d) | PVP, insoluble (Crospovidone) | 12.50 mg |
| (e) | PVP 90 | 1.00 mg |
| (f) | calcium stearate | 0.80 mg |
| | Total per core | 38.75 mg |

(a) is mixed with some of (b), (c) and (d). The remainder of (b) and (c) is added to the clear aqueous solution of (e) and adjusted to a pH of >10 using (b). Granulation is carried out in a fluidized bed granulator using this solution. The remainder of (d) and (f) is added to the dried granules and the granules are pressed in a suitable tablet machine.

| B. Coating | | | |
|---|---|---|---|
| | Ingredients | Initial weight | Coating per core |
| (g) | Eudragit RS 30 D | 2400.00 g | 4.876 mg |
| (h) | purified water | 4800.00 g | |
| (i) | propylene glycol | 144.00 g | 0.975 mg |
| (j) | Ca stearate | 21.60 g | 0.146 mg |
| (k) | 1 N NaOH | 81.10 g | 0.002 mg |
| | Total film coating | 7446.70 g | 6.000 mg |

The ingredients are stirred to give a dispersion which is screened before processing. The dispersion is sprayed onto the cores obtained under A in a suitable apparatus.

The coating application of 6 mg per tablet core leads to a spontaneously commencing and complete release of active compound after 2 hours.

Example 2

Combinations

The following combinations of tablets according to the invention (prepared according 10 Example 1, comprising 10 mg of active compound, below "tablet E") and the known enteric tablets (prepared according to EP-B-589981, comprising 10 mg of active compound, below "tablet M") are, for example, conceivable, the tablets being dispensed into hard gelatin capsules of size 3:

1 tablet E+1 tablet M 2 tablets E+2 tablets M 3 tablets E+1 tablet M 1 tablet E+3 tablets M Instead of the enteric tablets, the pellets prepared according to EP-B-589981 can also be used.

COMMERCIAL APPLICABILITY

The oral administration forms according to the invention can be employed for the treatment and prevention of all the diseases which are considered to be treatable or avoidable by the use of pyridin-2-ylmethylsulfinyl-1H-benzimidazoles. In particular, the oral administration forms according to the invention can be employed in the treatment of disorders of the stomach.

Surprisingly, sustained (i.e. more or less constant over a relatively long period) release behavior is not achieved using the oral administration forms according to the invention—despite the use of a customary sustained-release coating. On the contrary, initially no active compound at all is released over a certain period, the length of this period—as explained above—being controllable by the type and thickness of the membrane.

After expiry of the adjustable period, all of the active compound is then released within a very short space of time. Due to the dissolution of the particles embedded in the membrane, the membrane becomes porous or, due to the swelling of the permeable membrane, this becomes permeable and water penetrates into the core; as a result of this the tablet disintegrant begins to swell, and when the swelling pressure is sufficient in order to disintegrate the membrane, the active compound is released spontaneously and completely.

With the aid of the oral administration form according to the invention, it is thus possible to simulate an administration of active compound at a later time. As a result, the possibility is opened up of allowing a once daily administration instead of a twice daily administration of the active compound to begin by combining, for example, in one and the same administration form (e.g. in a capsule) two active cornpound forms whose release is different (e.g. a customary, enteric tablet and a tablet according to the invention).

The invention therefore further relates to the combination of an oral administration form according to the invention with a conventional (i.e. enteric-coated) administration form for pyridin-2-ylmethylsulfinyl-1H-benzimidazoles. "Combination" in this connection is understood as meaning the fixed or free combination.

In the fixed combination, both administration forms are present in a single dose unit (e.g. In a common tablet of outer conventional construction and inner core coated according to the invention, in a capsule comprising conventionally coated pellets and pellets according to the invention, or in particular in a capsule comprising two or more tablets, of which at least one corresponds to the specification according to the invention).

In the free combination, the two administration forms (that according to the invention and the conventional one) are present in separate dose units, which can be contained in a common packaging unit or in separate packaging units. In a common packaging unit, the different administration forms, for example, can be arranged in the form of capsules or tablets in rows lying next to one another in a blister pack. At the time indicated by the physician, the patient would in each case successively take a capsule or tablet from each row within a short length of time (in particular within 5 minutes).

Independently of whether a fixed or free combination is present, the compliance in the case of the combination according to the invention is in any case considerably greater than when two conventional administration forms have to be taken in a relatively large space of time (for example in the space of 3 to 12 hours).

The two-fold administration of active compound simulated by the fixed or free combination leads in a relatively large space of time (compared with the same dose of active compound as a single administration) to a smaller width of variation in the active compound blood levels in the patients and moreover to more rapid symptom relief.

In this connection, the fixed combination is preferred, particularly the combination of pellets according to the invention and conventional pellets and very particularly the combination of tablets according to the invention and conventional tablets in one capsule.

The treatment dose for an adult patient is, with respect to the pyridin-2-ylmethylsulfinyl-1H-benzimidazoles or their pharmaceutically tolerable salts, approximately 5 mg to 100 mg, in particular 10 mg to 80 mg, preferably 20 mg to 40 mg per day, calculated on the free acid. This treatment dose can be evenly or unevenly divided over the two administration forms in the combination according to the invention. A more or less equal division is preferred, e.g. 20 mg of the administration form according to the invention and 20 mg of the conventional (enteric-coated) administration form, in each case based on the free acid.

For their part, the oral administration forms according to the invention or the combinations according to the invention can in turn be combined with other medicaments, in particular with antimicrobial agents, such as are employed for the control of the bacterium *Helicobacter pylori* (*H. pylori*). Suitable antimicrobial agents for the control of the bacterium *H. pylori* which may be mentioned are bismuth salts [e.g. bismuth subcitrate, bismuth subsalicylate, ammonium bismuth(III) potassium citrate dihydroxide, bismuth nitrate oxide, dibismuth tris(tetraoxodialuminate)], but in particular β-lactam antibiotics, for exampie penicillins (such as benzylpenicillin, phenoxymethylpenicillin, propicillin, azidocillin, didoxacillin, flucloxacillin, oxacillin, amoxycillin, bacampicillin, ampicillin, mezlocillin, piperacillin or azlocillin), cephalosporins (such as cefadroxil, cefaclor, cefalexin, cefixime, cefuroxime, cefatamet, cefadroxil, ceftibuten, cefpodoxime, cefotetan, cefazolin, cefoperazone, ceftizoxime, cefotaxime, ceftazidime, cefamandol, cefepime, cefoxitin, cefodizime, cefsulodin, ceftriaxone, cefotiam or cefinenoxime) or other β-lactam antibiotics (e.g. aztreonam, loracarbef or meropenem); enzyme inhibitors, for example sulbactam; tetracyclines, for example tetracycline, oxytetracycline, minocycline or doxycycline; aminoglycosides, for example tobramycin, gentamicin, neomycin, streptomycin, amikacin, netilmicin, paromomycin or spectinomycin; amphenicols, for example chloramphenicol or thiamphenicol; lincomycins and macrolide antibiotics, for example clindamycin, lincomycin, erythromycin, clarithromycin, spiramycin, roxithromycin or azithromycin; polypeptide antibiotics, for example colistin, polymixin B, telcoplanin or vancomycin; gyrase inhibitors, for example norfloxacin, cinoxacin, ciprofloxacin, pipemidic acid, enoxacin, nalidixic acid, pefloxacin, fleroxacin or ofloxacin; nitroimidazoles, for example metronidazole; or other antibiotics, for example fosfomycin or fusidic acid, where these antibacterially active substances—together with the oral administration forms according to the invention or with the combinations according to the invention—can be administered on their own or alternatively combined with one another. Combinations of antibacterially active substances which may be mentioned are, for example, amoxicillin plus metronidazole, clarithromycin plus metronidazole and amoxicillin plus clarithromycin.

The invention claimed is:

1. An oral fixed combination administration form for an active compound, which is pyridine-2-ylmethylsulfinyl-1H-benzimidazole or a pharmaceutically acceptable salt thereof, which comprises the active compound in a capsule in two different administration forms, which release the active compound at two different points of time, wherein one administration form comprises the active compound together with a tablet disintegrant and bears a sustained-release coating film comprising a water-insoluble and physiologically tolerable plastic membrane having low swelling power in water and in which small soluble particles are embedded, and wherein the other administration form comprises the active compound and bears an enteric coating film.

2. An oral fixed combination administration form as claimed in claim 1, wherein the pyridine-2-ylmethylsulfinyl-1H-benzimidazole is pantoprazole.

3. An oral fixed combination administration form as claimed in claim 2, wherein each administration form is in pellet form.

4. An oral fixed combination administration form as claimed in claim 2, wherein each administration form is in tablet form.

5. An oral fixed combination administration form as claimed in claim 2, wherein the tablet disintegrant is crospovidone.

6. An oral fixed combination administration form as claimed in claim 2, wherein the sustained-release coating film is a copolymer of acrylic and methacrylic acid esters having quaternary ammonium structures.

7. An oral fixed combination administration form as claimed in claim 2, which is suitable for once daily administration of pantoprazole or a pharmaceutically acceptable salt thereof instead of a twice daily administration.

8. A method of treating an amenable disorder of the stomach which comprises administering to a subject in need of such therapy an effective amount of an oral fixed combination administration form as claimed in claim 1.

9. A method of treating an amenable disorder of the stomach which comprises administering to a subject in need of such therapy an effective amount of an oral fixed combination administration form as claimed in claim 2.

10. A method of treating an amenable disorder of the stomach which comprises administering to a subject in need of such therapy an effective amount of an oral fixed combination administration form as claimed in claim 3.

11. A method of treating an amenable disorder of the stomach which comprises administering to a subject in need of such therapy an effective amount of an oral fixed combination administration form as claimed in claim 4.

12. A method of treating an amenable disorder of the stomach which comprises administering to a subject in need of such therapy an effective amount of an oral fixed combination administration form as claimed in claim 5.

13. A method of treating an amenable disorder of the stomach which comprises administering to a subject in need of such therapy an effective amount of an oral fixed combination administration form as claimed in claim 6.

14. A method of treating an amenable disorder of the stomach which comprises administering to a subject in need of such therapy an effective amount of an oral fixed combination administration form as claimed in claim 7.

15. An oral fixed combination administration form according to claim 1 wherein the administration form which comprises the active compound together with a tablet disintegrant releases said active compound only after gastric passage.

16. An oral fixed combination administration form according to claim 1 wherein the administration form which comprises the active compound together with a tablet disintegrant releases said active compound, once release thereof has commenced, within a short space of time, so that a rapidly rising and high active compound blood level is achieved.

17. An oral fixed combination administration form according to claim 1 wherein the administration form which comprises the active compound together with a tablet disintegrant releases said active compound after gastric passage spontaneously and completely.

18. An oral fixed combination administration form according to claim 1 wherein the administration form is that of a pharmaceutically acceptable salt selected from the group consisting of a calcium salt, a potassium salt and a sodium salt.

19. An oral fixed combination administration form according to claim 1 wherein the tablet disintegrant is a member selected from the group consisting of a cellulose derivative, a starch, sodium carboxymethylstarch, bentonite, sodium alginate, pectin and crosslinked polyvinylpyrrolidone.

20. An oral fixed combination administration form according to claim 1 wherein the tablet disintegrant is sodium carboxymethylcellulose or potato starch.

21. An oral fixed combination administration form according to claim 1 wherein each administration form has a core which contains a further auxiliary, filler, binder, stabilizer, or any combination thereof.

22. An oral fixed combination administration form according to claim 21 wherein the stabilizer is a pharmacologically tolerable alkali metal, alkaline earth metal or earth metal salt of a weak acid or a pharmacologically tolerable hydroxide or oxide of an alkaline earth metal or of an earth metal.

23. An oral fixed combination administration form according to claim 1, wherein the plastic membrane does not absorb more than 5% by weight of water in aqueous medium.

24. An oral fixed combination administration form according to claim 1, wherein the small soluble particles are lactose crystals.

25. An oral fixed combination administration form according to claim 1, wherein the small soluble particles are salts.

26. An oral fixed combination administration form according to claim 25, wherein the salts are ammonium salts.

27. An oral fixed combination administration form according to claim 26, wherein the ammonium salts are ester groups of a copolymer of acrylic and methacrylic acid esters having quaternary ammonium structure.

28. An oral fixed combination form according to claim 1, wherein the weight ratio of plastic to soluble particles is approximately 2:1 to 1:3.

29. An oral fixed combination administration form according to claim 28, wherein the weight ratio of plastic to soluble particles is 4:3 to 4:5.

30. A method of treating an amenable disorder of the stomach which comprises administering to a subject in need of such therapy an effective amount of an oral fixed combination administration form as claimed in claim 23.

31. A method of treating an amenable disorder of the stomach which comprises administering to a subject in need of such therapy an effective amount of an oral fixed combination administration form as claimed in claim 24.

32. A method of treating an amenable disorder of the stomach which comprises administering to a subject in need of such therapy an effective amount of an oral fixed combination administration form as claimed in claim 25.

33. A method of treating an amenable disorder of the stomach which comprises administering to a subject in need of such therapy an effective amount of an oral fixed combination administration form as claimed in claim 26.

34. A method of treating an amenable disorder of the stomach which comprises administering to a subject in need of such therapy an effective amount of an oral fixed combination administration form as claimed in claim 27.

35. A method of treating an amenable disorder of the stomach which comprises administering to a subject in need of such therapy an effective amount of an oral fixed combination administration form as claimed in claim 28.

36. A method of treating an amenable disorder of the stomach which comprises administering to a subject in need of such therapy an effective amount of an oral fixed combination administration form as claimed in claim 29.

* * * * *